US011464508B2

(12) United States Patent
Courtwright et al.

(10) Patent No.: US 11,464,508 B2
(45) Date of Patent: Oct. 11, 2022

(54) ACTUATOR RETAINER FOR SURGICAL STAPLER

(71) Applicant: ETHICON LLC, Guaynabo, PR (US)

(72) Inventors: Nicholas D. Courtwright, Villa Hills, KY (US); Barry Thomas Jamison, Fairfield, OH (US); Michael S. Cropper, Edgewood, KY (US); Bradley A. Arnold, Mason, OH (US)

(73) Assignee: Cilag GmbH International, Zug (CH)

( * ) Notice: Subject to any disclaimer, the term of this patent is extended or adjusted under 35 U.S.C. 154(b) by 318 days.

(21) Appl. No.: 16/409,957

(22) Filed: May 13, 2019

(65) Prior Publication Data
US 2020/0360014 A1 Nov. 19, 2020

(51) Int. Cl.
*A61B 17/068* (2006.01)
*A61B 17/115* (2006.01)
(Continued)

(52) U.S. Cl.
CPC .......... *A61B 17/068* (2013.01); *A61B 17/115* (2013.01); *A61B 17/105* (2013.01);
(Continued)

(58) Field of Classification Search
CPC ... A61B 17/068; A61B 17/105; A61B 17/115; A61B 2017/0046; A61B 2017/07271; A61B 2017/07285; A61B 2017/0725
See application file for complete search history.

(56) References Cited

U.S. PATENT DOCUMENTS

| 4,633,874 A | * | 1/1987 | Chow | A61B 17/07207 227/176.1 |
| 5,156,614 A | | 10/1992 | Green et al. | |

(Continued)

FOREIGN PATENT DOCUMENTS

WO    WO 2015/065482 A1    5/2015

OTHER PUBLICATIONS

European Search Report and Written Opinion dated Jul. 27, 2020 for Application No. EP 20174180.8, 10 pgs.
(Continued)

*Primary Examiner* — Anna K Kinsaul
*Assistant Examiner* — Daniel Jeremy Leeds
(74) *Attorney, Agent, or Firm* — Frost Brown Todd LLC

(57) ABSTRACT

A surgical stapler includes a first elongate member, a second elongate member, a clamp member, and a firing assembly. The first elongate member includes a distal portion that supports an anvil surface that includes a plurality of staple forming pockets. The second elongate member includes a distal portion that is configured to receive a staple cartridge. The clamp member is operable to releasably clamp the first elongate member against the second elongate member. The firing assembly is translatable from a first longitudinal position to a second longitudinal position to fire the staple cartridge. The firing assembly includes a slider and an actuator. The slider includes a first coupling feature. The actuator is configured to be selectively actuated by a user. The actuator includes a second coupling feature that is configured to generally surround the first coupling feature of the slider when the actuator moves relative to the slider.

20 Claims, 15 Drawing Sheets

(51) Int. Cl.
*A61B 17/10* (2006.01)
*A61B 17/00* (2006.01)
*A61B 17/072* (2006.01)

(52) U.S. Cl.
CPC .............. *A61B 2017/0046* (2013.01); *A61B 2017/0725* (2013.01); *A61B 2017/07257* (2013.01); *A61B 2017/07271* (2013.01); *A61B 2017/07285* (2013.01)

(56) References Cited

U.S. PATENT DOCUMENTS

| | | | |
|---|---|---|---|
| 5,718,359 A | 2/1998 | Palmer et al. | |
| 7,658,312 B2* | 2/2010 | Vidal | A61B 17/282 227/178.1 |
| 7,905,381 B2 | 3/2011 | Baxter, III et al. | |
| 7,954,686 B2 | 6/2011 | Baxter, III et al. | |
| 8,348,129 B2 | 1/2013 | Bedi et al. | |
| 8,540,129 B2 | 9/2013 | Baxter, III et al. | |
| 8,540,133 B2 | 9/2013 | Bedi et al. | |
| 8,789,740 B2 | 7/2014 | Baxter, III et al. | |
| 9,289,211 B2* | 3/2016 | Williams | A61B 17/07207 |
| 9,381,017 B2 | 7/2016 | Chen et al. | |
| 2013/0306703 A1* | 11/2013 | Ehrenfels | A61B 17/105 227/175.2 |
| 2017/0362379 A1* | 12/2017 | El-Hibri | C08G 75/23 |
| 2019/0239881 A1 | 8/2019 | Laurent et al. | |
| 2019/0239882 A1 | 8/2019 | McLain et al. | |
| 2019/0239883 A1 | 8/2019 | Baxter, III et al. | |
| 2019/0239884 A1 | 8/2019 | Baxter, III et al. | |
| 2019/0239885 A1 | 8/2019 | Stokes et al. | |
| 2019/0239886 A1 | 8/2019 | Jones et al. | |
| 2020/0046350 A1 | 2/2020 | Deck et al. | |

OTHER PUBLICATIONS

International Search Report and Written Opinion dated Jul. 29, 2020 for Application No. PCT/IB2020/054249, 13 pgs.
U.S. Appl. No. 16/410,006, entitled "Actuator Support Structure for Surgical Stapler," filed May 13, 2019.

* cited by examiner

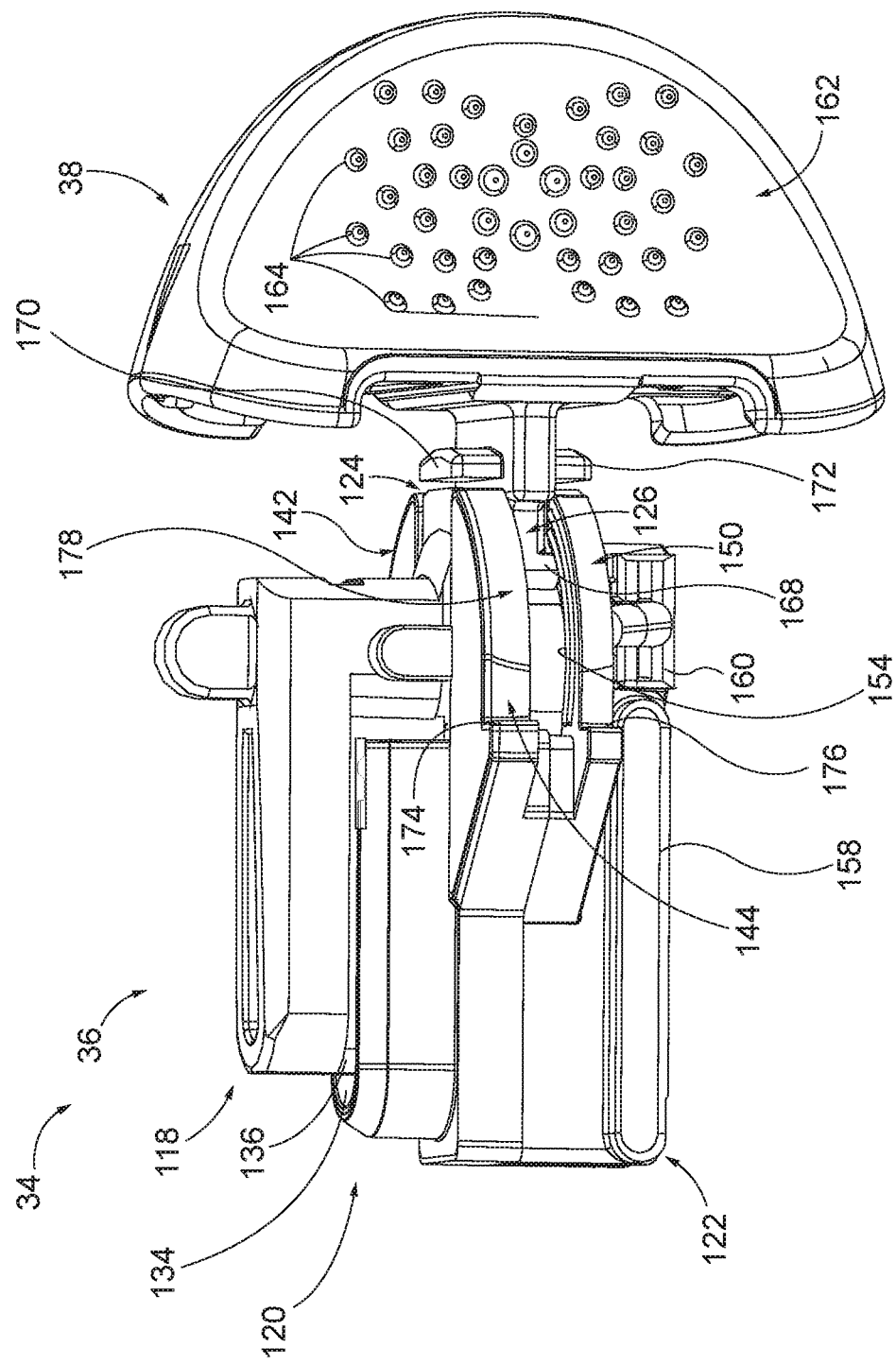

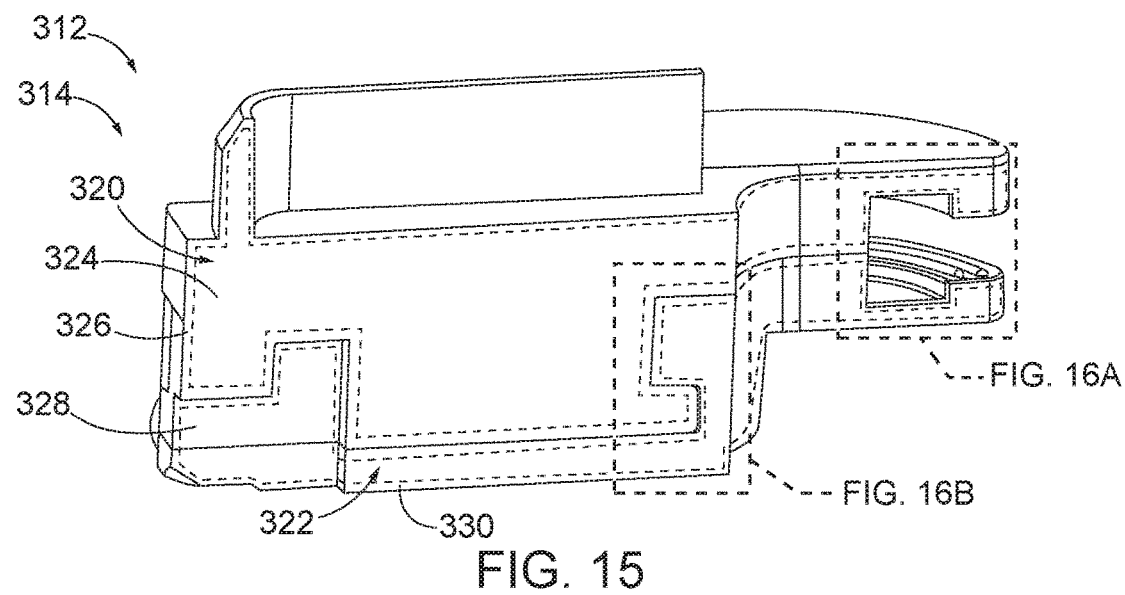
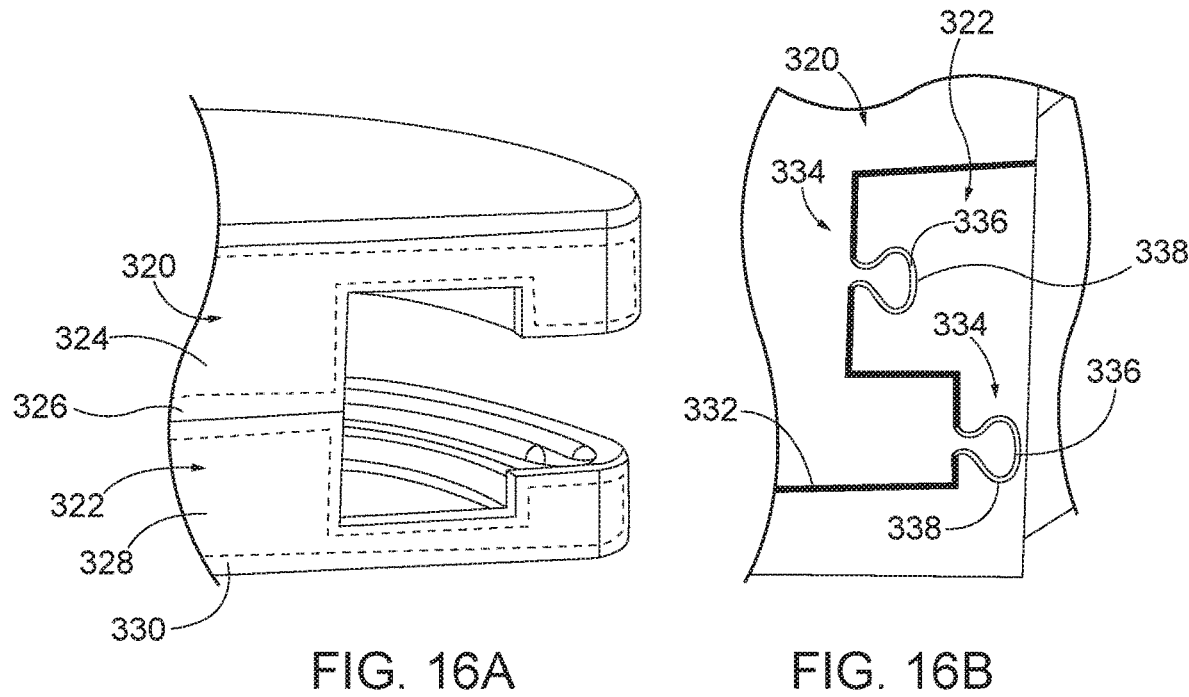

ACTUATOR RETAINER FOR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6 depicts a perspective view of a firing assembly of the linear surgical stapler of FIG. 1 that includes a central body portion, upper and lower body portions, and the actuator;

FIG. 15 depicts a cross-sectional perspective view of a second exemplary alternative firing assembly that includes upper and lower body portions, where upper and lower body portions include first and second substrates overmolded with first and second casings;

FIG. 16A depicts an enlarged cross-sectional perspective view of an enlarged portion 16A of FIG. 15 showing the first and second substrates overmolded with the first and second casings; and FIG. 16B depicts an enlarged cross-sectional perspective view of an enlarged portion 16B of FIG. 15 showing a securement feature disposed between upper and lower body portions.

Figure 1:
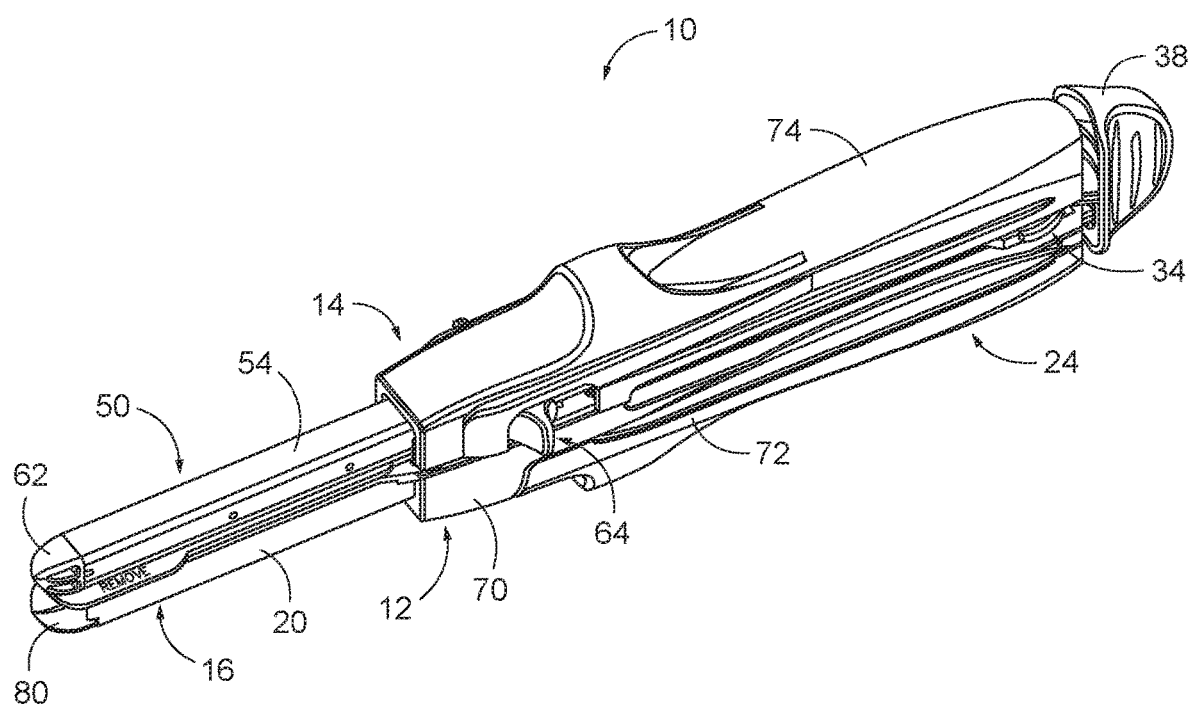
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
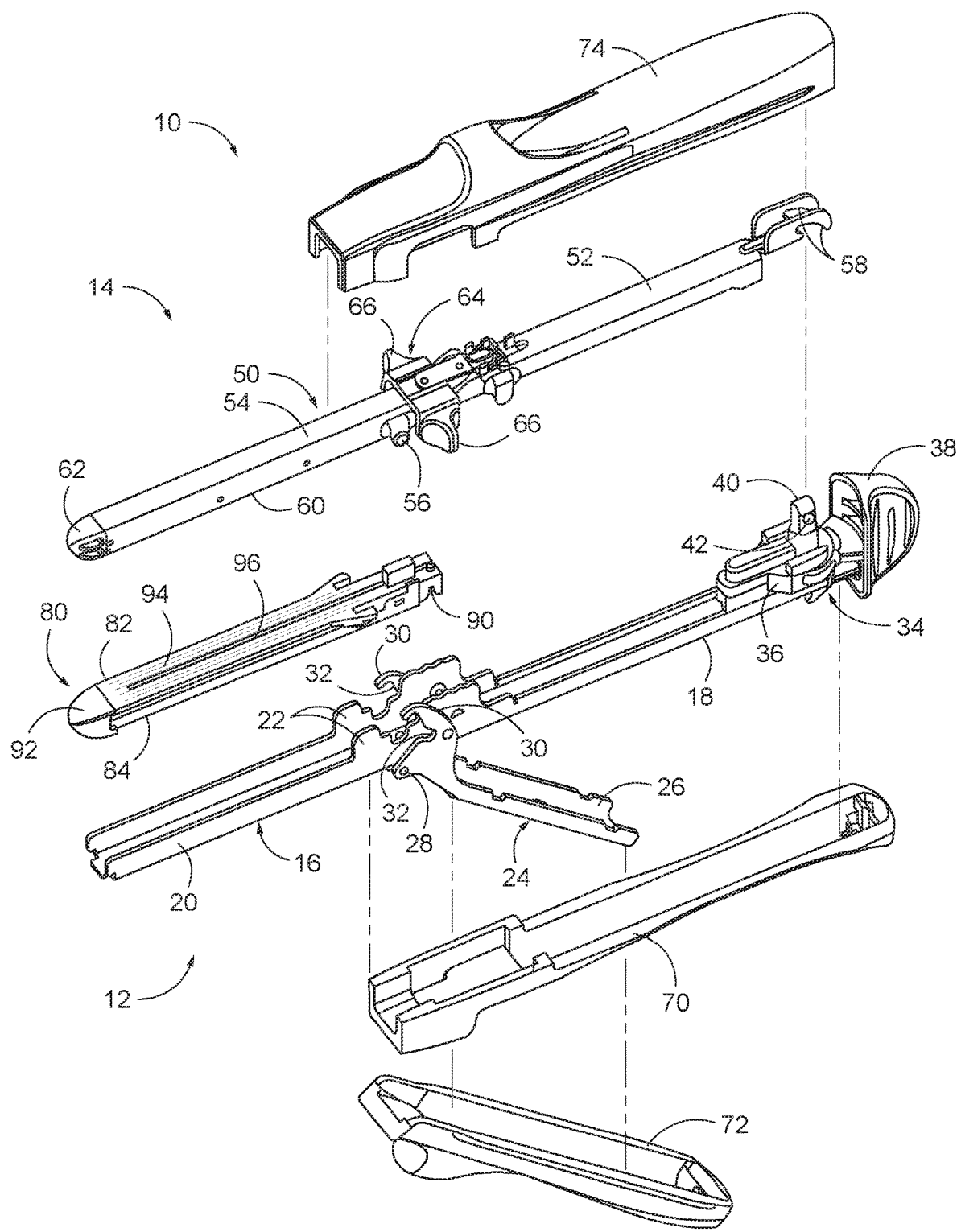
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes an elongate cartridge channel (16) having a proximal frame portion (18) that slidably retains a portion of a firing assembly (34), a distal jaw portion (20) that supports a staple cartridge (80) (or "reload"), and a pair of upright side flanges (22) arranged medially therebetween.

Cartridge half (12) further includes a clamp lever (24) pivotably coupled to an underside of cartridge channel (16) in approximate alignment with side flanges (22). Clamp lever (24) includes an elongate lever arm (26) having a free proximal end and a distal end that is pivotably coupled to cartridge channel (16) with a pivot pin (28). A pair of opposed jaws (30) extends distally from the distal end of lever arm (26) alongside flanges (22) of cartridge channel (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to cartridge channel (16) between open and closed positions to releasably clamp anvil half (14) against cartridge half (12) and thereby capture tissue layers therebetween.

As shown best in FIG. 2, firing assembly (34) of cartridge half (12) includes a slider (36), shown schematically, slidably retained within proximal frame portion (18) of cartridge channel (16), an actuator (38) (or "firing knob") movably coupled with slider (36), and an elongate actuating beam (not shown) extending distally from slider (36) and configured to couple with a sled (100) (shown in FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
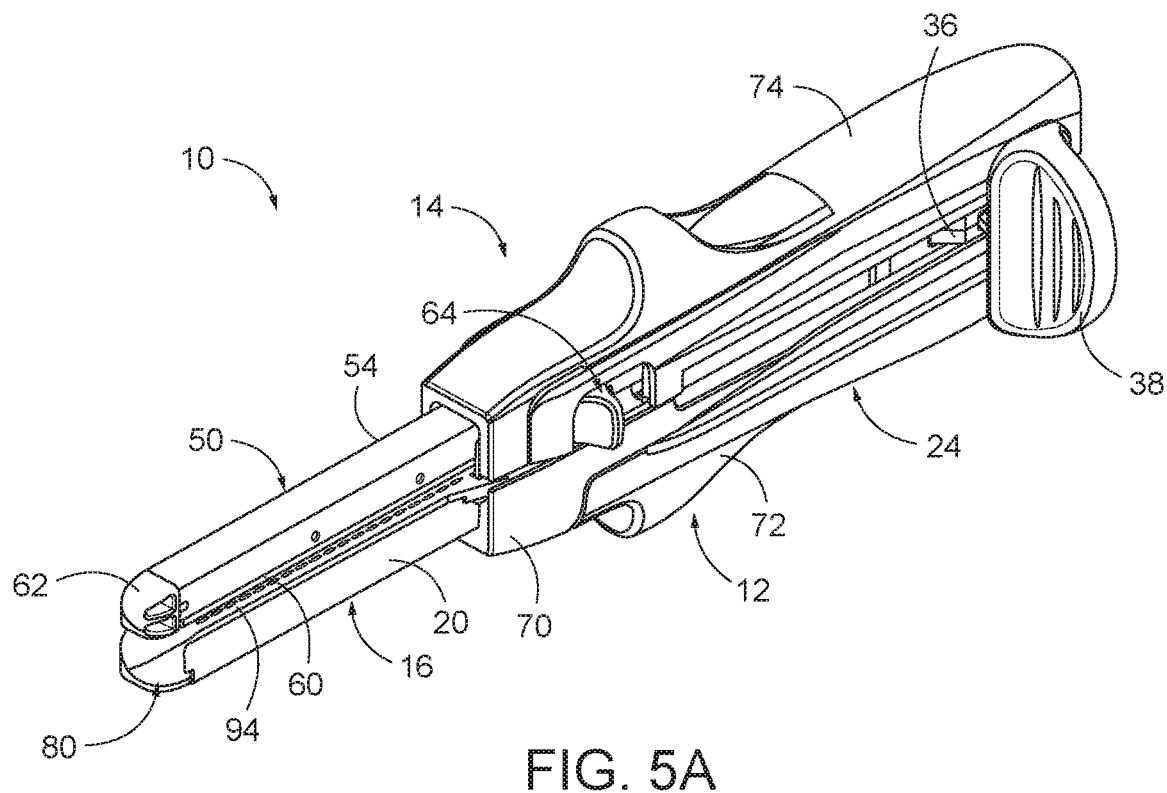
FIG. 5A depicts a distal perspective view of the linear surgical stapler of FIG. 1, showing an actuator of the stapler in a proximal, pre-fired position.
Figure 5B:
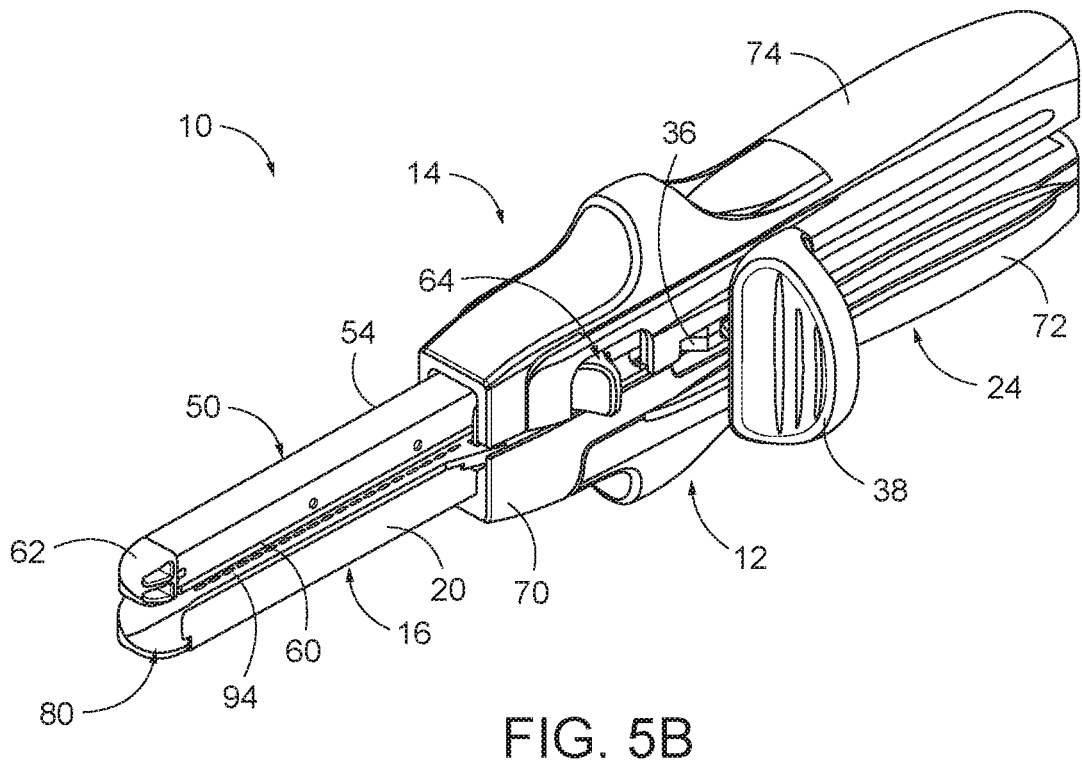
FIG. 5B depicts a distal perspective view of the linear surgical stapler of FIG. 1, showing the actuator in a distal, fired position.

Slider (36) is configured to be translatably driven within proximal frame portion (18) by actuator (38) between a proximal home position shown in FIGS. 2 and 5A, and a distal fired position shown in FIG. 5B. In the proximal home position, slider (36) abuts a post (40) fixed at a proximal end of cartridge channel (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion (52) and are configured to releasably capture opposed lateral ends of proximal pivot pin (42) of cartridge half (12). Distal jaw portion (54) supports an anvil surface in the form of an anvil plate (60) having a plurality of staple forming pockets (not shown), and additionally supports a distal tip member (62). In other versions of stapler (10), the anvil surface may be formed integrally with or otherwise be rigidly connected to distal jaw portion (54) of anvil channel (50).

Anvil half (14) of the present example further includes a staple height adjustment mechanism (64) mounted to a medial portion of anvil channel (50). Staple height adjustment mechanism (64) is operatively coupled with anvil plate (60), for example via one or more camming features (not shown), and includes a pair of user-engageable projections (66). Longitudinal adjustment of projections (66) between a plurality of predetermined positions causes anvil plate (60) to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown best in in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes a first shroud (70) that covers an outwardly facing side of proximal frame portion (18) of cartridge channel (16). Cartridge half (12) further includes a second shroud (72) that covers an outwardly facing side of clamp lever (24) and is configured to pivot with clamp lever (24) relative to cartridge channel (16) and first shroud (70). Anvil half (14) includes a third shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

Figure 3:
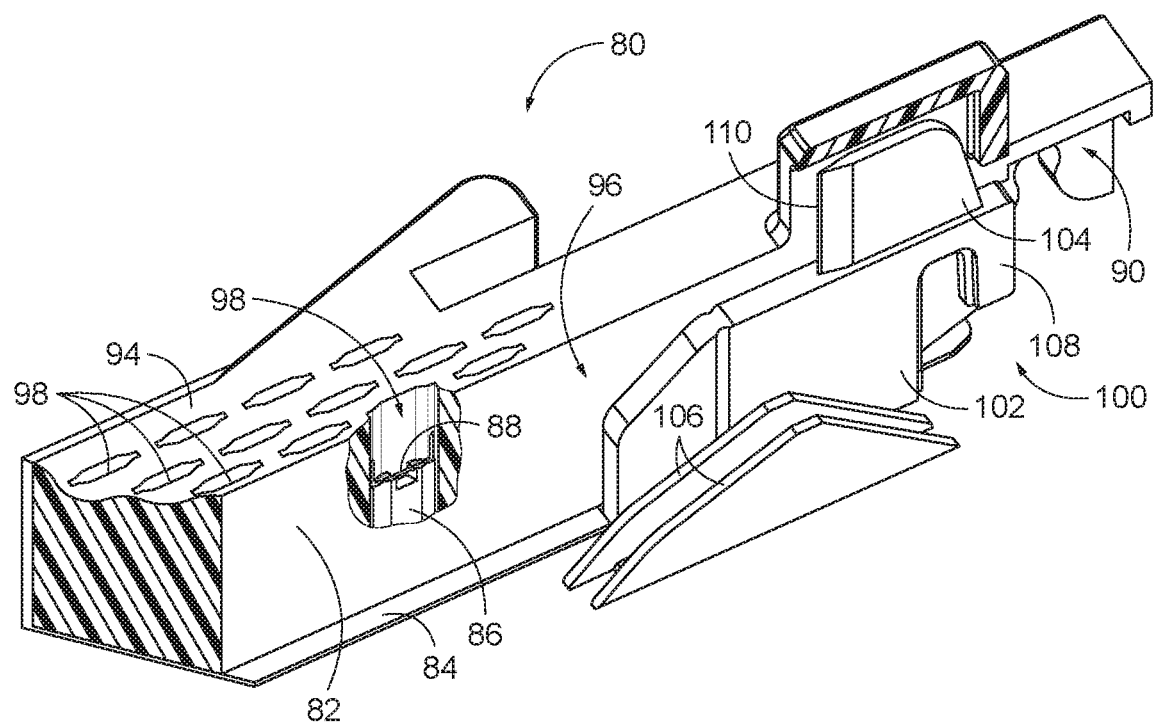
FIG. 3 depicts a cross-sectional perspective view of a staple cartridge assembly of the linear surgical stapler of FIG. 1.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having coupling features (90) configured to releasably engage corresponding coupling features (not shown) of distal jaw portion (20) of cartridge channel (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and staple (88). As shown in FIG. 3, an interior of cartridge body (82) slidably houses sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple forming pockets of anvil plate (60). In this manner, distal actuation of firing assembly (34) provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
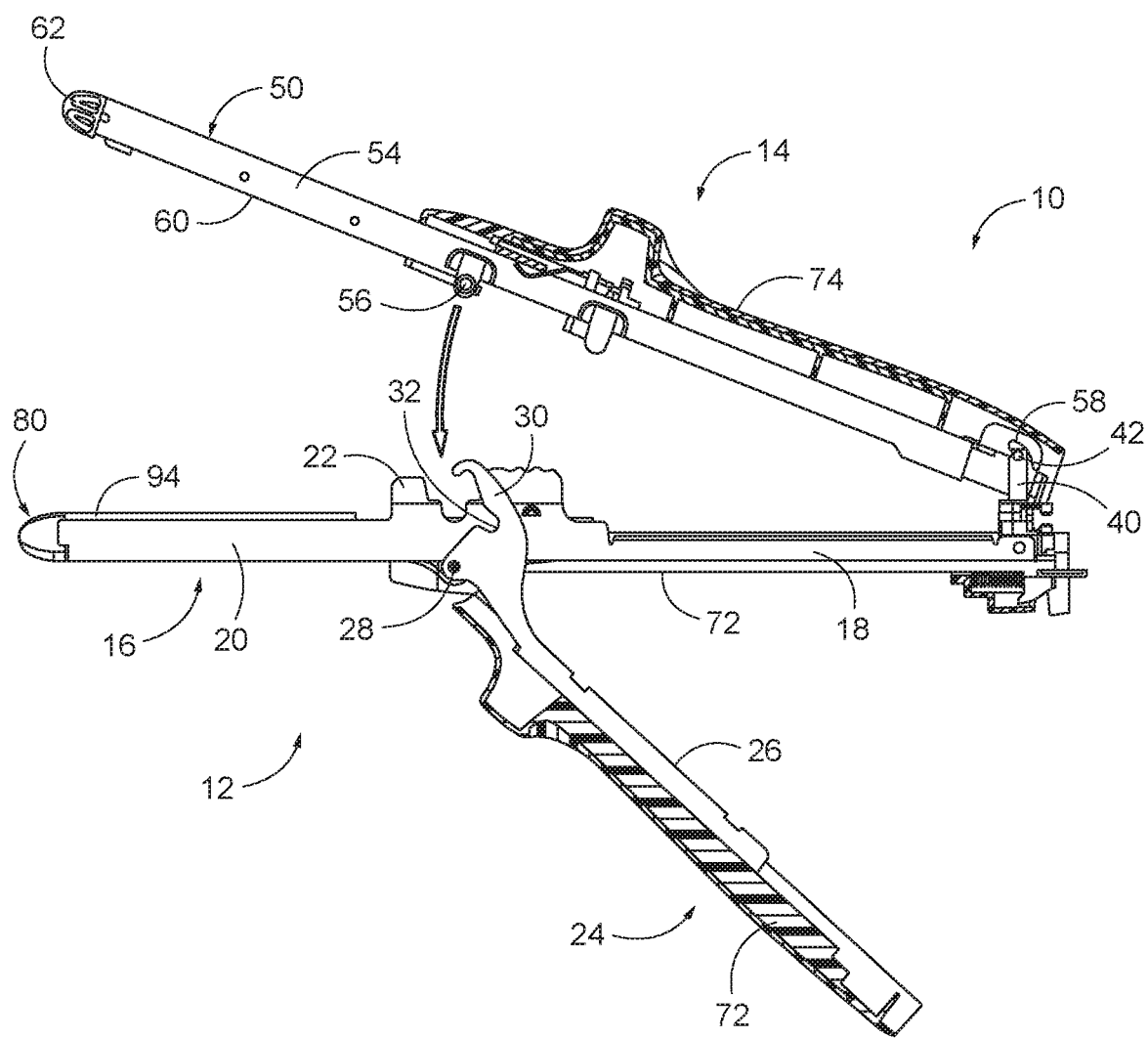
FIG. 4A depicts a cross-sectional side view of the linear surgical stapler of FIG. 1, showing the stapler halves coupled together at their proximal ends with the clamp lever in an open position.
Figure 4B:
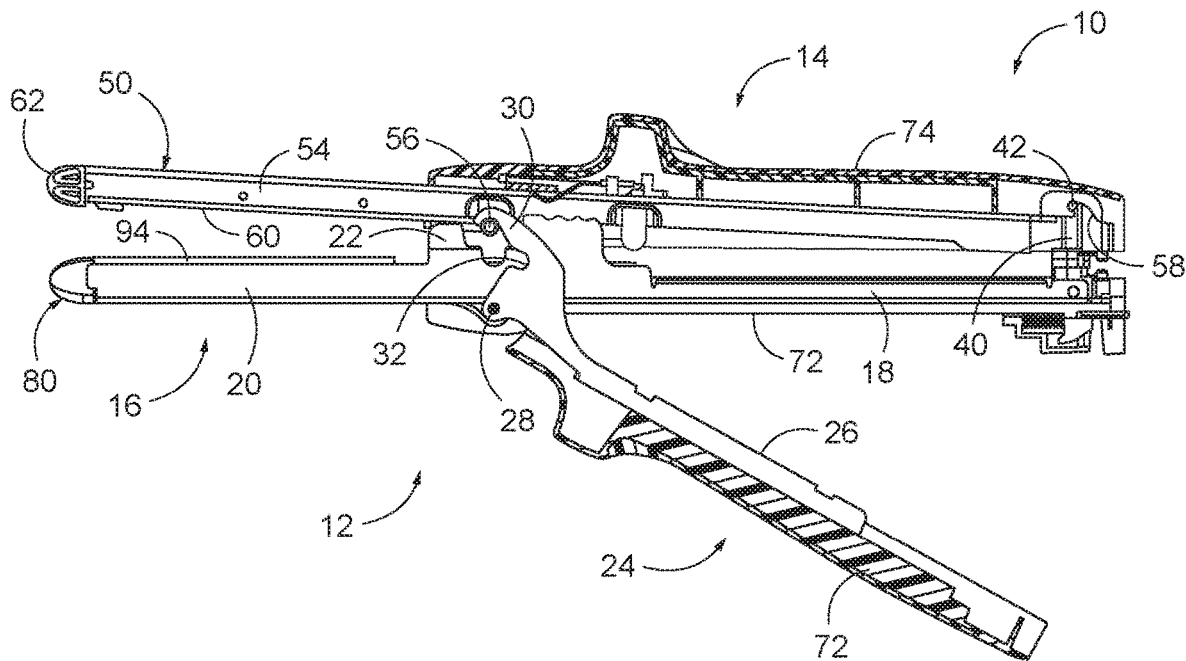
FIG. 4B depicts a cross-sectional side view of the linear surgical stapler of FIG. 1, showing the stapler halves coupled together with the clamp lever in a partially closed position.
Figure 4C:
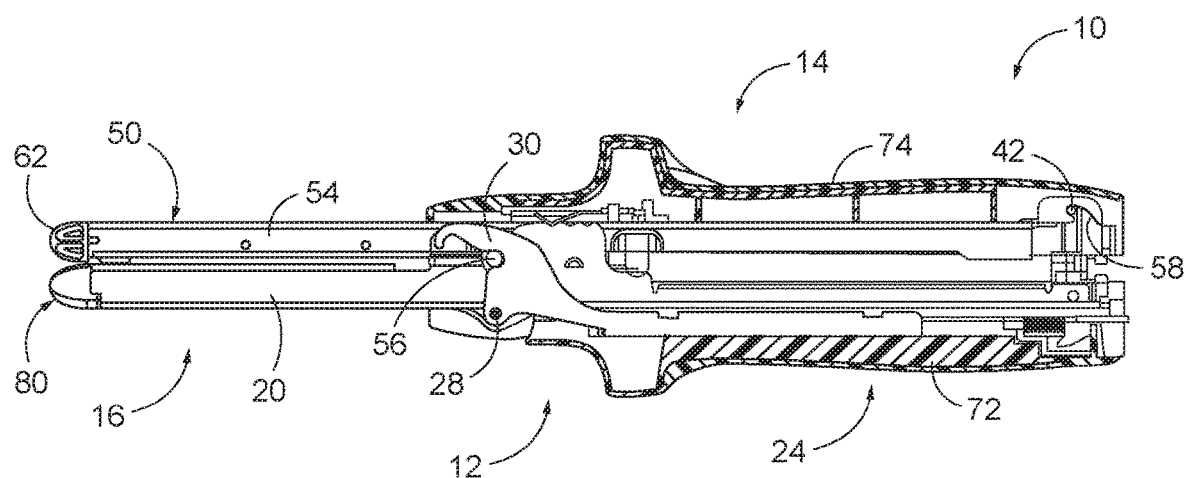
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

C. Exemplary Firing Assembly

Figure 7:
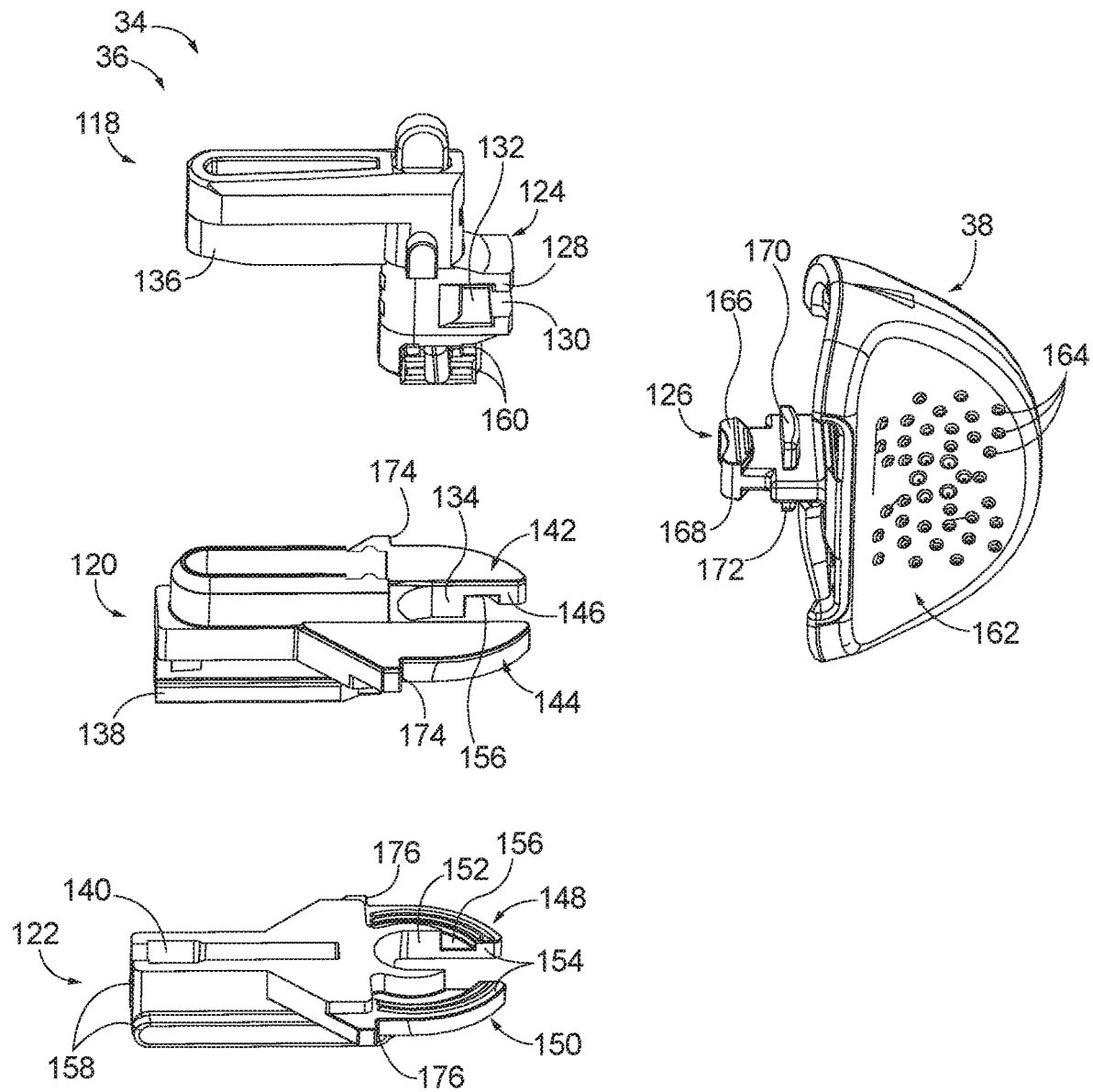
FIG. 7 depicts an exploded perspective view of the firing assembly of FIG. 6.

FIGS. 6-10 show details of firing assembly (34) of linear surgical stapler (10) of FIG. 2. As previously described with reference to FIGS. 5A-5B, firing assembly (34) is translatable from a first longitudinal position to a second longitudinal position to fire staple cartridge (80) when first elongate member (shown as anvil half (14)) is clamped against second elongate member (shown as cartridge half (12)). FIG. 7 shows a perspective view of firing assembly (34) of FIG. 2. As shown, firing assembly (34) includes slider (36) and actuator (38).

Slider (36) includes a central body portion (118), and first and second body portions (shown as upper and lower body portions (120, 122)). As shown in FIG. 6, central body portion (118) includes a C-shaped coupling feature (124)

that engages a distal coupling feature (126) of actuator (38). C-shaped coupling feature (124) includes first and second opposing retention features (128, 130) that are shown as being vertically oriented. C-shaped coupling feature (124) forms a cavity (132) that receives distal coupling feature (126) of actuator (38).

Upper and lower body portions (120, 122) are configured to slide longitudinally into central body portion (118) to collectively form slider (36). Upper body portion (120) includes a longitudinal slot (134) (shown in FIG. 7) configured to receive distal projection (136) of central body portion (118). Upper body portion (120) includes a lower distal projection (138) (shown in FIG. 7) configured to be received within a distal slot (140) of lower body portion (122). Upper body portion (120) includes first and second arms (142, 144) that are separated by longitudinal slot (134). Longitudinal slot (134) is configured to receive central body portion (118). First and second arms (142, 144) of upper body portion (120) include retention features (146) configured to securably receive and retain distal coupling feature (126) of actuator (38).

Figure 8:
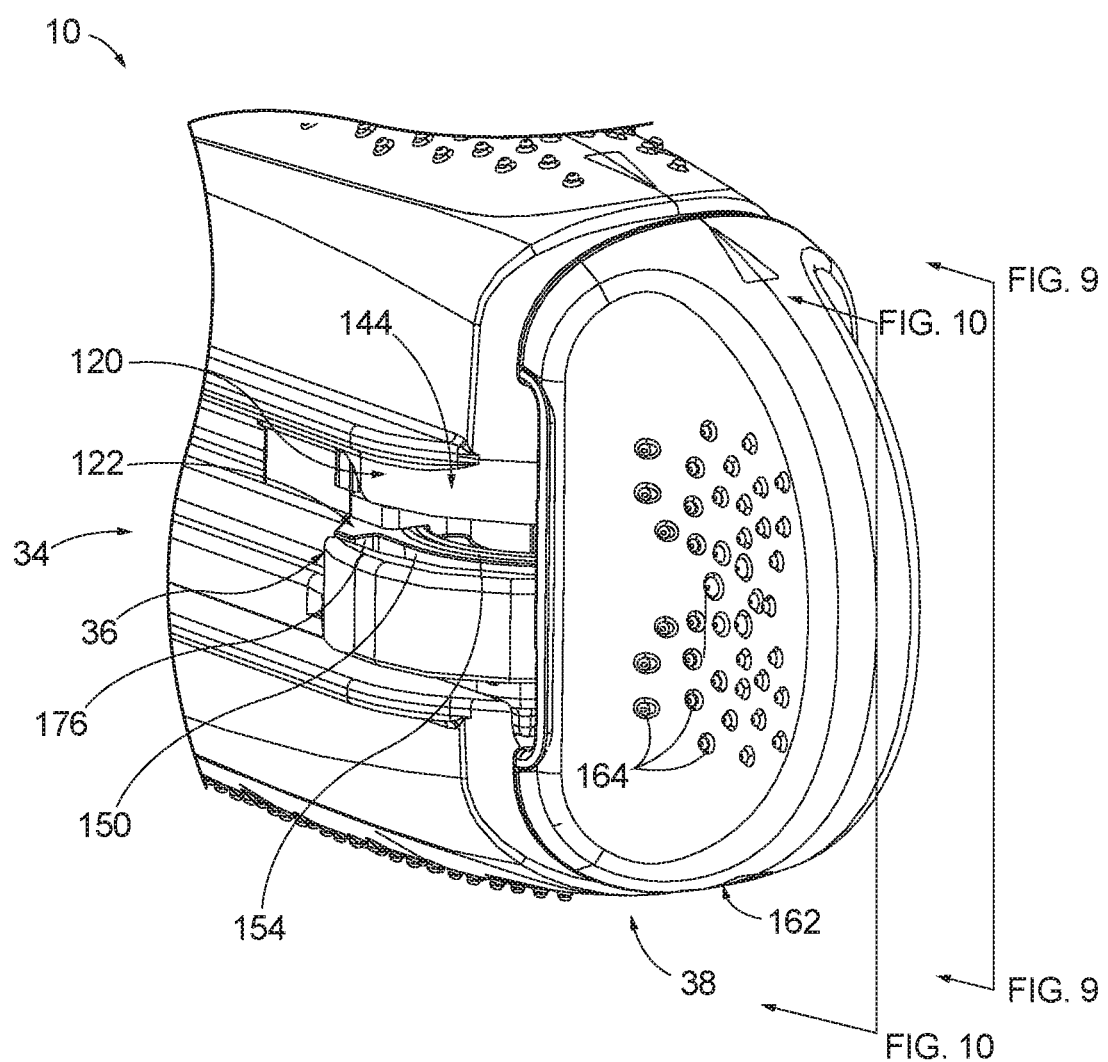
FIG. 8 depicts a proximal perspective view of a proximal portion of the linear surgical stapler of FIG. 1, but with the actuator in a proximal-most position.

Similarly, lower body portion (122) includes first and second arms (148, 150) that are separated by a longitudinal slot (152) (shown in FIG. 7). Longitudinal slot (152) is configured to receive central body portion (118). First and second arms (148, 150) of lower body portion (122) include retention features (154) configured to securably receive and retain distal coupling feature of actuator (38). Retention features (146, 154) of upper and lower body portions (120, 122) define a cavity (156) that captures distal coupling feature (126) of actuator (38). As shown in FIGS. 7-8, lower body portion (122) includes lower rails (158) and central body portion (118) includes lower rails (160). Lower rails (158, 160) are configured to slide along a track (not shown) to vertically guide slider (36) when moved distally.

As shown in FIGS. 6-8, actuator (38) includes a body (162) that may include gripping features (164). As previously described, actuator (38) may transmit force applied by the user to firing assembly (34) to perform a transection of tissue. Distal coupling feature (126) of actuator (38) extends distally from body (162) of actuator (38). Distal coupling feature (126) includes first and second opposing distal curved projections (166, 168) and first and second opposing proximal projections (170, 172). As shown, first and second opposing distal curved projections (166, 168) and first and second opposing proximal projections (170, 172) extend vertically. Actuator (38) may be rotated relative to slider (36) until actuator (38) contacts a stop feature (174) of upper body portion (120) and a stop feature (176) of lower body portion (122).

Figure 9:
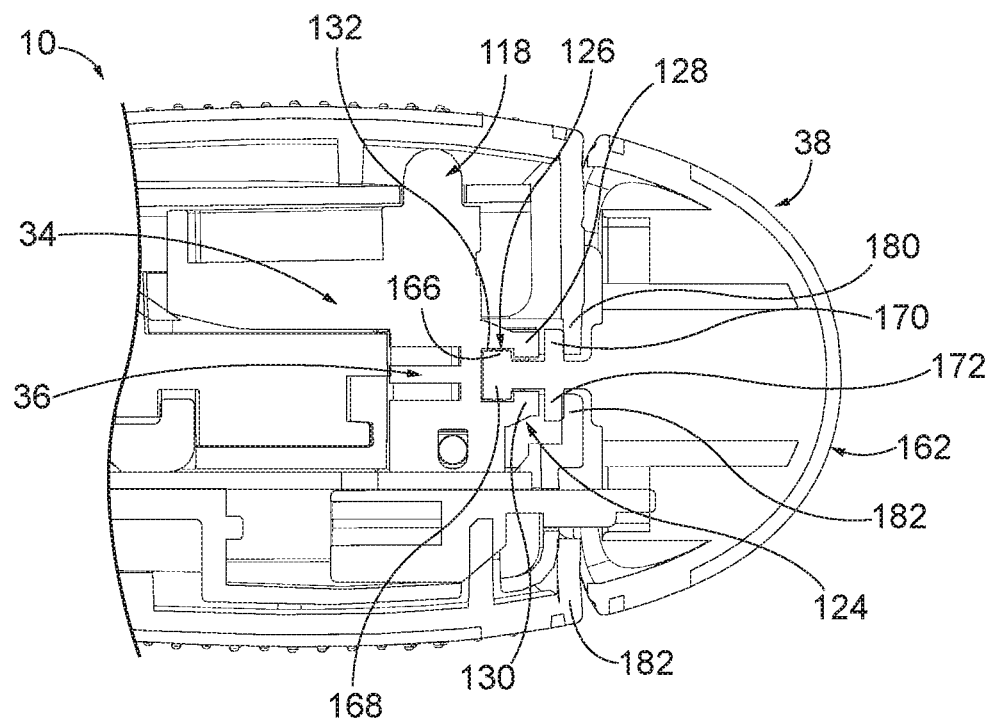
FIG. 9 depicts a cross-sectional view of the linear surgical stapler of FIG. 8, taken along line 9-9 of FIG. 8, showing the firing assembly of FIG. 6 as including a center body portion that includes a C-shaped coupling feature that is engaged with a distal coupling feature of the actuator.
Figure 10:
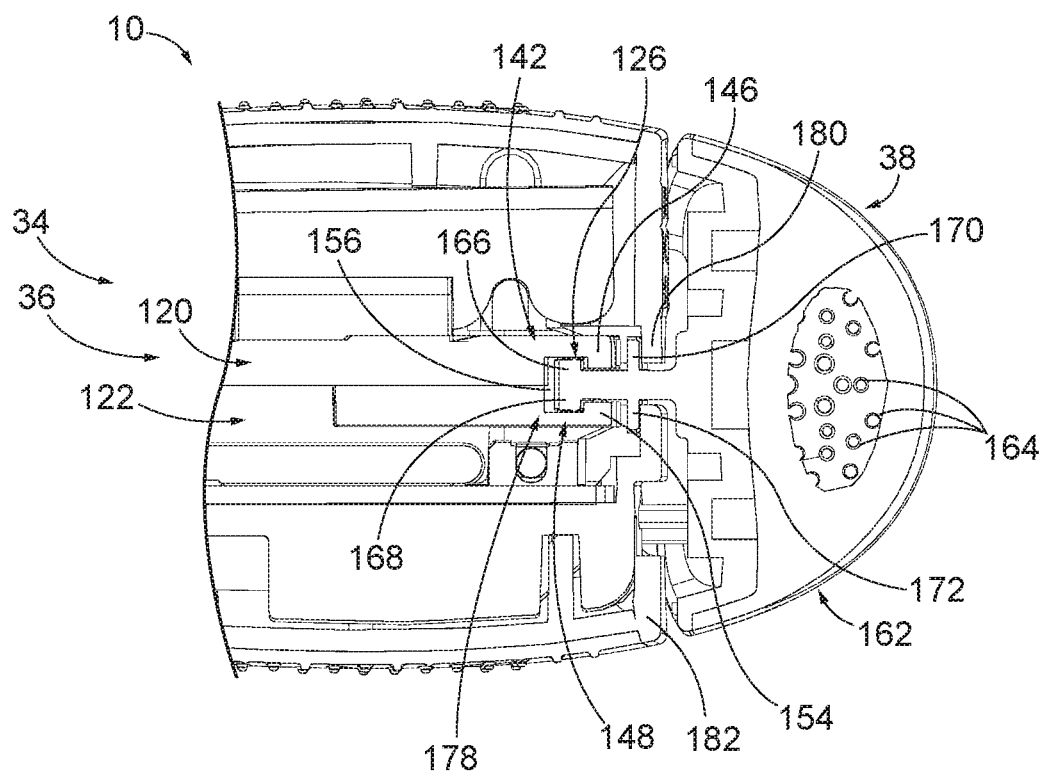
FIG. 10 depicts a cross-sectional view of the linear surgical stapler of FIG. 8, taken along line 10-10 of FIG. 8, showing upper and lower body portions collectively forming a C-shaped coupling feature that is engaged with the distal coupling feature of the actuator.

FIG. 8 shows a proximal perspective view of a proximal portion of linear surgical stapler (10) of FIG. 1, but with actuator (38) in a proximal-most position. FIGS. 9-10 show two respective cross-sections of linear surgical stapler (10). Particularly, FIG. 9 shows a cross-sectional view of linear surgical stapler (10) of FIG. 8, taken along line 9-9 of FIG. 8, where C-shaped coupling feature (124) of central body portion (118) is engaged with distal coupling feature (126) of actuator (38). Similarly, FIG. 10 shows a cross-sectional view of linear surgical stapler (10) of FIG. 8, taken along line 10-10 of FIG. 8, where a C-shaped coupling feature (178) collectively formed by upper and lower body portions (120, 122) are engaged with distal coupling feature (126) of actuator (38). As such, C-shaped coupling feature (124) of central body portion (118) and C-shaped coupling feature (178) collectively formed by upper and lower body portions (120, 122) create cavities (132, 156) that are aligned to provide a track to prevent distal coupling feature (126) of actuator (38) from detaching. As shown, first shroud (70) includes a retention feature (180) that is disposed proximal to first proximal projection (170) to prevent first proximal projection (170) of actuator (38) from moving proximally. Similarly, third shroud (74) includes a retention feature (182) that is disposed proximal to second proximal projection (172) to prevent second proximal projection (172) of actuator (38) from moving proximally.

II. Exemplary Linear Surgical Stapler Having Exemplary Alternative Firing Assembly In situations where the user applies an off-centered load to actuator (38) of linear surgical stapler (10), high torsional forces are applied to individual components of firing assembly (34). The high torsional forces may cause deflection of the individual components of firing assembly (34), which may allow the individual components to separate from one another. For example, these individual components may include upper and lower body portions (120, 122). Particularly, high torsional forces may cause deflection of first and second arms (142, 144) of upper body portion (120) and/or first and second arms (148, 150) of upper body portion (120). This deflection may provide an opportunity for actuator (38) to detach from slider (36), which is undesirable. As a result, it may be desirable to strengthen the interface of slider (36) and actuator (38) to prevent, or at least minimize, the deflection of the individual components of firing assembly (34).

As described in greater detail below with reference to FIGS. 11-16B, exemplary firing assemblies (212, 312) and related strengthening methods may limit localized stresses and related deflections within firing assembly (212, 312) when surgeon-applied, off-center loading creates a torsional load within firing assembly (212, 312). These firing assemblies (212, 312) and related strengthening methods enable the individual components of firing assemblies (212, 312) to remain in close proximity to each other and behave as an integrated system rather than individual components during high firing force scenarios. For example, as described below with reference to FIGS. 11-14, the interface of the individual components of firing assembly (34) may be transformed to strengthen firing assembly (212), thus minimizing undesirable deflection of firing assembly (212). More specifically, as described below with reference to FIGS. 15-16B, firing assembly (312) may strengthen the interface between the individual components of firing assembly (34) by adding one or more strengthening features.

A. First Exemplary Alternative Firing Assembly

FIGS. 11-14A show an exemplary linear surgical stapler (210) (or "linear cutter") that includes a first exemplary alternative firing assembly (212) instead of firing assembly (34). Linear surgical stapler (210) is generally similar to linear surgical stapler (10) described above, except as where otherwise described below. Similar to linear surgical stapler (10), linear surgical stapler (210) includes a first elongate member (shown previously as anvil half (14)), a second elongate member (shown previously as cartridge half (12)), and a clamp member (shown previously as clamp lever (24)). As previously described with reference to linear surgical stapler (10), anvil half (14) has a distal portion (shown previously as distal jaw portion (54)) that supports an anvil surface (shown as anvil plate (60)), where anvil plate (60) includes a plurality of staple forming pockets. As previously described with reference to linear surgical stapler (10), cartridge half (12) includes a distal portion (shown as distal jaw portion (20)) configured to receive staple cartridge (80), and clamp lever (24) is operable to releasably clamp anvil half (14) against cartridge half (12).

Figure 11:
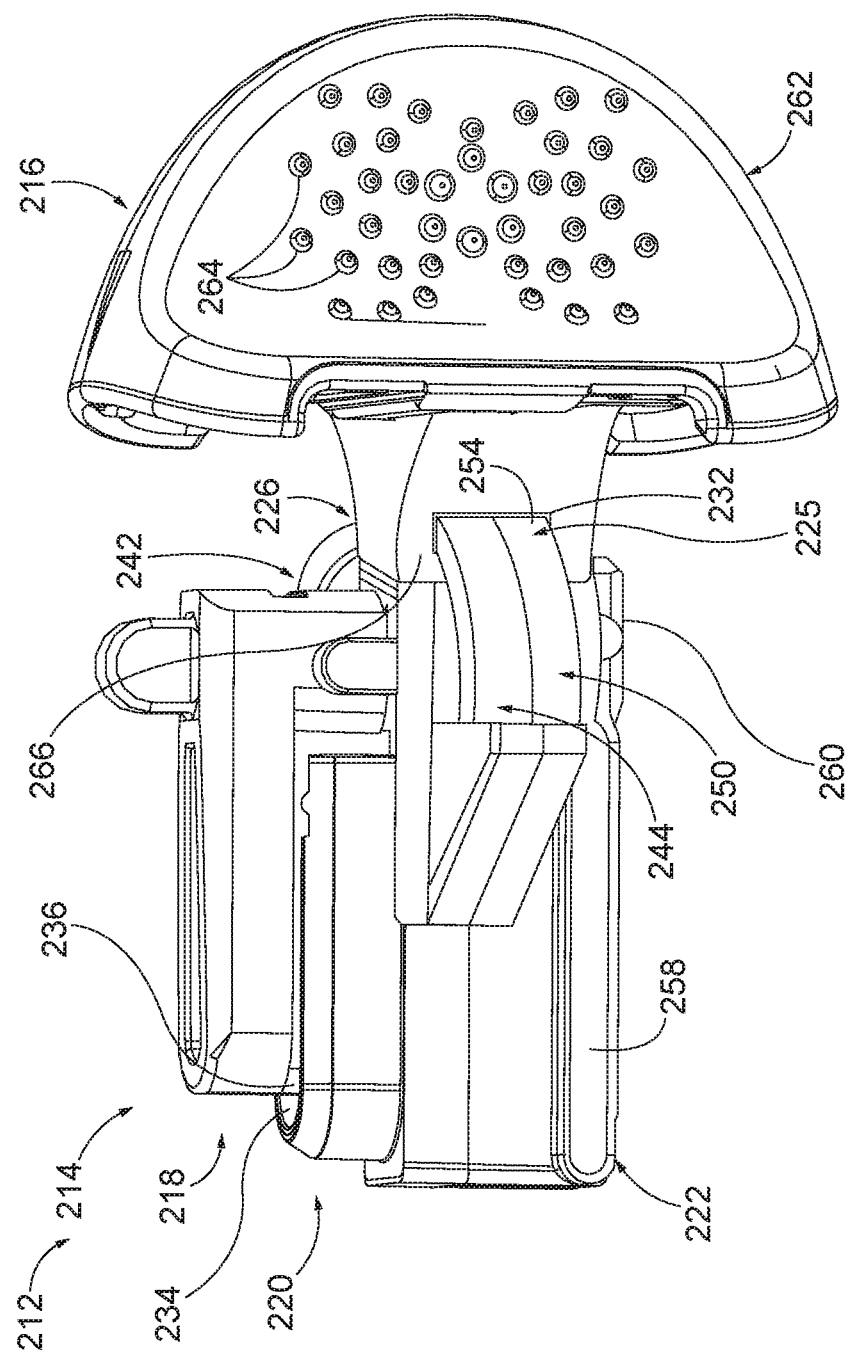
FIG. 11 depicts a perspective view of an alternative exemplary firing assembly that includes a central body portion, upper and lower body portions, and an actuator.
Figure 12:
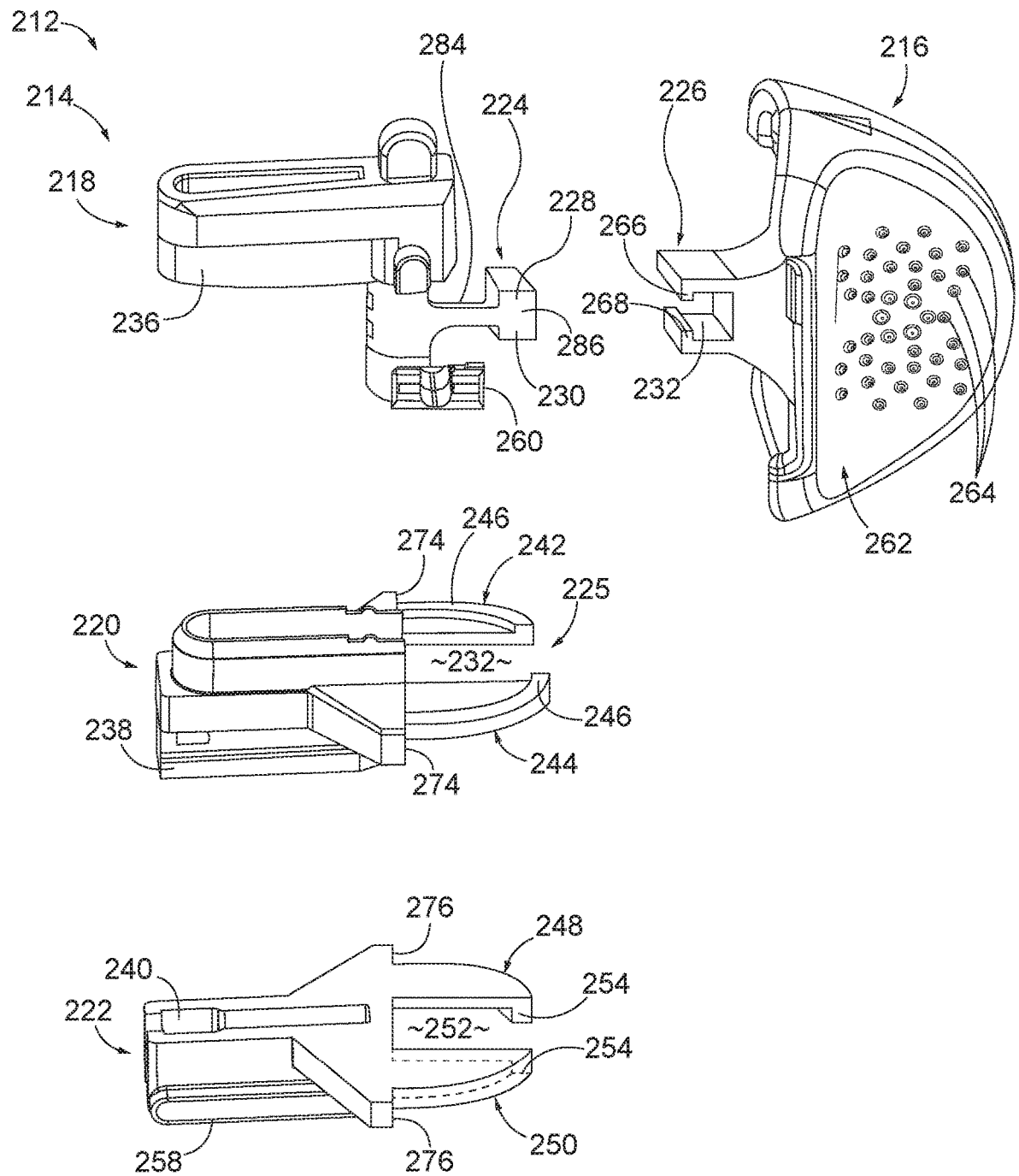
FIG. 12 depicts an exploded perspective view of the firing assembly of FIG. 11.

FIG. 11 shows a perspective view of firing assembly (212), and FIG. 12 shows an exploded perspective view of firing assembly of FIG. 11. Similar to firing assembly (34), firing assembly (212) is translatable from a first longitudinal position to a second longitudinal position to fire staple cartridge (80) when anvil half (14) is clamped against cartridge half (12). Firing assembly (212) includes a slider (214) and an actuator (216). As shown in FIGS. 11-12, slider (214) includes a central body portion (218), and first and second body portions (shown as upper and lower body portions (220, 222)).

Figure 13:
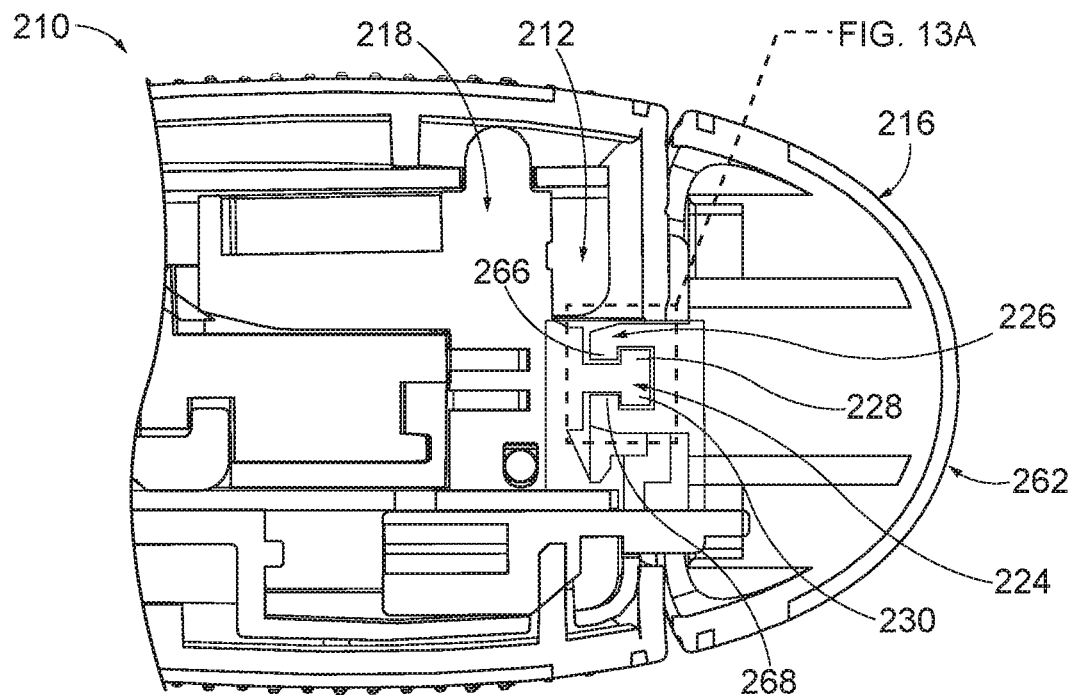
FIG. 13 depicts a cross-sectional view of a linear surgical stapler similar to FIG. 7, but including the firing assembly of FIG. 11, where a proximal coupling feature of the center body portion is engaged with a distal coupling feature of the actuator.
Figure 13A:
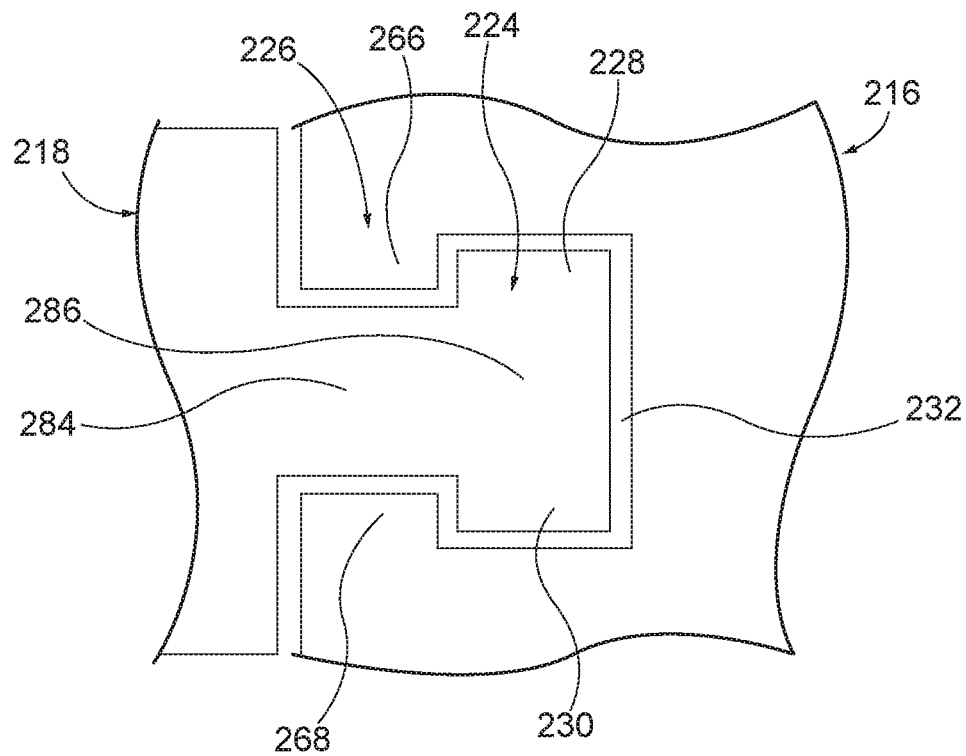
FIG. 13A depicts an enlarged portion 13A of FIG. 13, where the coupling feature of the central body portion is engaged with the distal coupling feature of the actuator.
Figure 14:
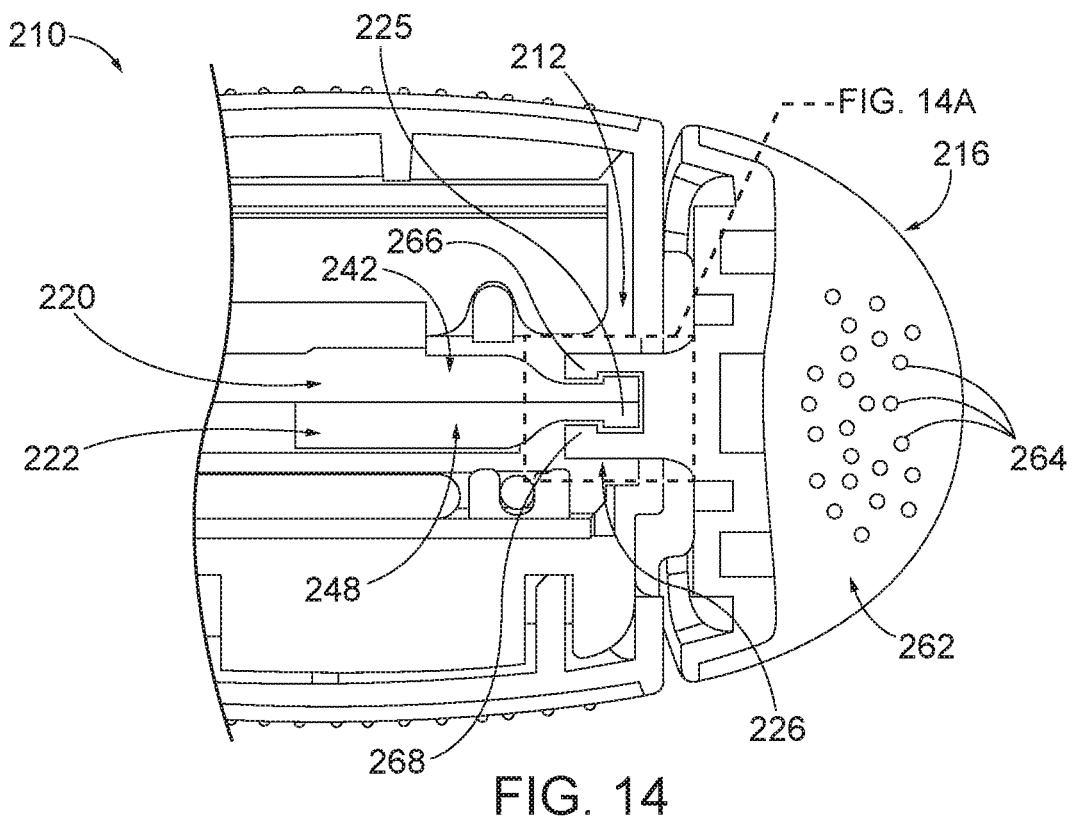
FIG. 14 depicts a cross-sectional view of a linear surgical stapler similar to FIG. 8, but including the firing assembly of FIG. 11, where a proximal coupling feature collectively formed by the upper and lower body portions is engaged with the distal coupling feature of the actuator.
Figure 14A:
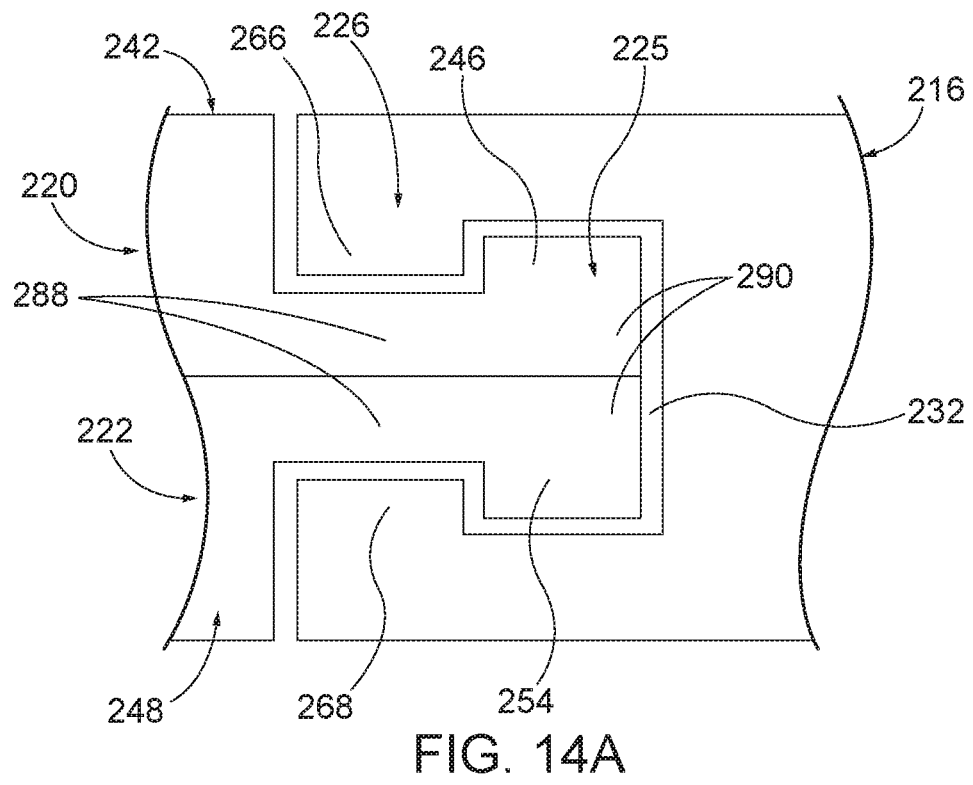
FIG. 14A depicts an enlarged portion 14A of FIG. 13, where the proximal coupling feature of the upper and lower body portions is engaged with the distal coupling feature of the actuator.

Central body portion (218) is similar to central body portion (118) and is described in greater detail below with reference to FIGS. 11-13A. Central body portion (218) includes a proximal coupling feature (224) that engages a distal coupling feature (226) of actuator (216). FIGS. 12-13B show proximal coupling feature (224) as including first and second opposing projections (228, 230). FIG. 13 shows a cross-sectional view of a linear surgical stapler (210) similar to FIG. 7, but including firing assembly (212) of FIG. 11. As shown, proximal coupling feature (224) of central body portion (218) is engaged with distal coupling feature (226) of actuator (216). Unlike C-shaped coupling feature (124) of central body portion (118) described above, proximal coupling feature (224) of central body portion (218) is not C-shaped. FIG. 13A shows an enlarged portion 13A of FIG. 13. Instead, distal coupling feature (226) of actuator (216) is shown as being C-shaped, forming a C-shaped coupling feature of actuator (216). As shown in FIGS. 13 and 13A, first and second opposing projections (228, 230) of proximal coupling feature (224) are vertically oriented. More specifically, first projection (228) of central body portion (218) faces a first direction (e.g. upward), and second projection (230) of central body portion (218) faces a second direction that is opposite first direction (e.g. downward). Alternatively, first and second opposing projections (228, 230) may be disposed at an angle from vertical. Proximal coupling feature (224) may be integrally formed as a unitary piece together with central body portion (218).

Actuator (216) is similar to actuator (38) and is described in greater detail below with reference to FIGS. 11-14A. Actuator (216) is configured to be selectively actuated by a user to slide slider (214). Actuator (216) includes a body (262) that may include gripping features (264). Actuator (216) may be used to transmit force applied by the user to firing assembly (212) to perform a transection of tissue. It is envisioned that firing assembly (212) may include, among other features, slider (214) and a pair of actuators (not shown) that are pivotably coupled with slider (214) to provide dual-sided firing of linear surgical stapler (210). Firing assembly (212) may be configured in accordance with at least some of the teachings of U.S. patent application Ser. No. 16/102,164, entitled "Firing System for Linear Surgical Stapler," filed on even date herewith, issued as U.S. Pat. No. 10,898,187 on Jan. 26, 2021, the disclosure of which is incorporated by reference herein.

Actuator (216) includes distal coupling feature (226) that is configured to limit vertical movement of first and second opposing projections (228, 230). Distal coupling feature (226) of actuator (216) extends distally from body (262) of actuator (216). Distal coupling feature (226) forms a cavity (232) that is shown as being generally enclosed, and receives proximal coupling feature (224) of central body portion (218). As shown, distal coupling feature (226) includes first and second opposing retention features (266, 268), which are shown as being vertically oriented. Relative spacing between first and second opposing retention features (266, 268) enables cavity (232) to securely receive proximal coupling feature (224) within cavity (232) and prevent proximal coupling feature (224) from exiting cavity (232). Particularly, cavity (232) receives first and second opposing projections (228, 230) of central body portion (218). It is also envisioned that distal coupling feature (226) of actuator (216) may have different shapes and/or sizes, such that distal coupling feature (226) still generally surrounds proximal coupling feature (224) when actuator (216) moves (e.g. rotates about a vertical axis) relative to slider (214). Distal coupling feature (226) is integrally formed together as a unitary piece together with actuator (38); or formed separately from multiple pieces and subsequently combined together. For example, distal coupling feature (226) or the entire actuator (38) may be formed from polymeric material such as ultem HU1000. Actuator (216) may be rotated relative to slider (214) until actuator (216) contacts stop feature (274, 276) of upper and lower body portions (220, 222).

As shown in FIGS. 11-12, upper and lower body portions (220, 222) are configured to slide longitudinally into central body portion (218) to collectively form slider (214). Upper body portion (220) includes a longitudinal slot (234) configured to receive distal projection (236) of central body portion (218). Upper body portion (220) includes first and second arms (242, 244) that are separated by longitudinal slot (234), where longitudinal slot (234) is configured to receive central body portion (218). First and second arms (242, 244) of upper body portion (220) include retention features (246) that are received and retained by distal coupling feature (226) of actuator (216) within cavity (232) of distal coupling feature (226). However, unlike retention features (146) that face toward lower body portion (122), retention features (246) face away from lower body portion (222).

Lower body portion (222) includes first and second arms (248, 250) that are separated by a longitudinal slot (252) (shown in FIG. 12), where longitudinal slot (252) is configured to receive central body portion (218) similar to central body portion (118) and lower body portion (122) shown in FIGS. 6-10. First and second arms (248, 250) of lower body portion (222) include retention features (254) that are received and retained by distal coupling feature (226) of actuator (216) within cavity (232) of distal coupling feature (226). Unlike retention features (154) that face toward upper body portion (120), retention features (254) face away from upper body portion (220). In other words, unlike retention features (146, 154) of upper and lower body portions (120, 122) described above with reference to FIGS. 6-10 that define cavity (156) that captures distal coupling feature (126) of actuator (38), retention features (246, 254) of upper and lower body portions (220, 222) abut each other and face away from each other to collectively form a proximal coupling feature (225). For example, proximal coupling feature (225) or entire upper and lower body portions (220, 222) may be formed from polymeric material, such as ultem HU1000. As shown, retention features (246) of upper body portion (220) face a first direction (e.g. upward) and abut retention features (254) of lower body portion (222) that face a second direction that is opposite first direction (e.g. downward). In other words, retention features (246, 254) of upper and lower body portions (220, 222) collectively form proximal coupling feature (225), shown as to form a rib/spine, which is captured within cavity (256) by first and second opposing retention features (266, 268) of actuator (216).

As such, first and second opposing retention features (266, 268) are configured to securably receive and maintain proximal coupling feature (224) of central body portion (218) and proximal coupling feature (225) (that includes retention features (246, 254) of upper and lower body portions (220, 222)) within cavity (232). Relative spacing between first and second opposing retention features (266, 268) securably receive and maintain proximal coupling features (224) and proximal coupling feature (225). In other words, as shown in FIG. 13A, proximal coupling feature (224) includes a neck portion (284) and a head portion (286), where there neck portion (284) has a cross-sectional area that is less than the spacing between first and second opposing retention features (266, 268), and head portion (286) has a cross-sectional area that is greater than the spacing between first and second opposing retention features (266, 268). Similarly, proximal coupling feature (225) includes neck portions (288) and head portions (290), where there neck portions (288) have a combined cross-sectional area that is less than the spacing between first and second opposing retention features (266, 268), and head portions (290) have a combined cross-sectional area that is greater than the spacing between first and second opposing retention features (266, 268).

As shown in FIG. 12, upper body portion (220) includes a lower distal projection (238) configured to be received within a distal slot (240) of lower body portion (222). Alternatively, or in addition to, the coupling between lower distal projection (238) and distal slot (240), upper and lower body portions (220, 222) may be coupled together using at least one of an adhesive, a press-pin feature, or an ultrasonic weld. At least one of upper and lower body portions (220, 222) includes a metal substrate and a polymeric overmold. At least one of upper and lower body portions (220, 222) may be strengthened using metal injection molding (MIM). At least one of upper and lower body portions (220, 222) is strengthened by including strengthening features. For example, as shown in FIGS. 11-12, lower body portion (222) includes lower rails (258) and central body portion (218) includes lower rails (260). Lower rails (258, 260) are configured to slide along a track (not shown) to vertically guide slider (214) when moved distally.

B. Second Exemplary Alternative Firing Assembly

FIGS. 15-16B show a second exemplary alternative firing assembly (312) incorporated instead of firing assembly (34). While not shown, firing assembly (312) may include actuator (38) and central body portion (118) described above. Similar to firing assembly (34), firing assembly (312) is translatable from a first longitudinal position to a second longitudinal position to fire staple cartridge (80) when first elongate member (shown previously as anvil half (14)) is clamped against second elongate member (shown previously as cartridge half (12)).

FIG. 15 shows a cross-sectional perspective view of firing assembly (312) that includes a slider (314). Slider (314) includes first and second body portions (shown as upper and lower body portions (320, 322)). FIG. 16A shows an enlarged cross-sectional perspective view of FIG. 15. At least one of upper and lower body portions (320, 322) includes a metal substrate and a polymeric overmold. As shown, upper body portion (320) includes a first substrate (324) overmolded with a first casing (326). Similarly, lower body portion (322) includes a second substrate (328) overmolded with a second casing (330). For example, first and second substrates (324, 328) may be formed from a metallic material and first and second casings may be formed from a polymeric material. Upper and lower body portions (320, 322) are fixably coupled together. Slider includes a first coupling feature. At least one of upper and lower body portions (320, 322) is strengthened using metal injection molding (MIM). Metal injection molding (MIM) refers to any metalworking process where finely-powdered metal is mixed with a binder material to create a feedstock that is subsequently shaped and solidified using a molding process (such as injection molding). Metal injection molding allows for high volume, complex parts to be shaped. Additionally, the geometry of upper and lower body portions (320, 322) may be optimized to further increase strength.

FIG. 16B shows an enlarged cross-sectional perspective view where upper and lower body portions (320, 322) are strengthened using at least one strengthening feature. In other words, the interface between upper and lower body portions (320, 322) may be strengthened. This includes, but is not limited to, gluing upper and lower body portions (320, 322) together using an adhesive, adding one or more press-pin features between upper and lower body portions (320, 322), and/or adding one or more welding features to upper and lower body portions (320, 322) to promote ultrasonic welding. As shown, upper and lower body portions (320, 322) are strengthened together using an adhesive (332) and a press-pin feature (334). For example, upper body portion (320) is shown as including a press-pin (336) that is fixably received by a corresponding cavity (338) disposed in lower body portion (322).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; and (d) a firing assembly, wherein the firing assembly is translatable from a first longitudinal position to a second longitudinal position to fire the staple cartridge when the first elongate member is clamped against the second elongate member, wherein the firing assembly comprises: (i) a slider that includes a first coupling feature, and (ii) an actuator configured to be selectively actuated by a user, wherein the actuator includes a second coupling feature configured to generally surround the first coupling feature of the slider when the actuator moves relative to the slider.

EXAMPLE 2

The surgical stapler of Example 1, wherein the second coupling feature is a C-shaped coupling feature that includes a cavity, wherein the cavity is configured to receive the first coupling feature.

EXAMPLE 3

The surgical stapler of Example 2, wherein the C-shaped coupling feature includes first and second opposing retention features configured to securably receive and maintain the first coupling feature within the cavity.

EXAMPLE 4

The surgical stapler of Example 3, wherein relative spacing between the first and second opposing retention features of the C-shaped coupling feature are configured to securably receive and maintain the first coupling feature within the cavity.

EXAMPLE 5

The surgical stapler any one or more of Examples 2 through 4, wherein the C-shaped coupling feature is integrally formed together as a unitary piece.

EXAMPLE 6

The surgical stapler of any one or more of Examples 2 through 5, wherein the first coupling feature of the slider is configured to guide the C-shaped coupling feature between a first lateral side of the slider and a second lateral side of the slider.

EXAMPLE 7

The surgical stapler of any one or more of Examples 1 through 6, wherein the slider includes first and second body portions.

EXAMPLE 8

The surgical stapler of Example 7, wherein the first body portion is an upper body portion and the second body portion is a lower body portion.

EXAMPLE 9

The surgical stapler of any one or more of Examples 7 through 8, wherein the first coupling feature includes first and second coupling portions of the first and second body portions.

EXAMPLE 10

The surgical stapler of Example 9, wherein the second coupling feature is a C-shaped coupling feature that forms a cavity, wherein the first and second coupling portions include first and second opposing retention features that are received within the cavity of the second coupling feature.

EXAMPLE 11

The surgical stapler of Example 10, wherein the C-shaped coupling feature is configured to limit vertical movement of the first and second opposing retention features.

EXAMPLE 12

The surgical stapler any one or more of Examples 7 through 11, wherein at least one of the first and second body portions includes a metal substrate and a polymeric overmold.

EXAMPLE 13

The surgical stapler of any one or more of Examples 7 through 12, wherein the first and second body portions are coupled together using at least one of an adhesive, a press-pin feature, or an ultrasonic weld.

EXAMPLE 14

The surgical stapler of any one or more of Examples 7 through 12, wherein at least one ultrasonic weld is disposed between the first and second body portions.

EXAMPLE 15

The surgical stapler of any one or more of Examples 7 through 12, wherein at least one press-pin feature is disposed between the first and second body portions.

EXAMPLE 16

A surgical stapler comprising: (a) a first elongate member that includes a distal portion that supports an anvil surface, wherein the anvil surface includes a plurality of staple forming pockets; (b) a second elongate member that includes a distal portion configured to receive a staple cartridge; (c) a clamp member operable to releasably clamp the first elongate member against the second elongate member; and (d) a firing assembly, wherein the firing assembly is translatable from a first longitudinal position to a second longitudinal position to fire the staple cartridge when the first elongate member is clamped against the second elongate member, wherein the firing assembly comprises: (i) a slider comprising: (A) a first body portion that includes a first retention feature facing a first direction; and (B) a second body portion that includes a second retention feature facing a second direction that is opposite the first direction, and (ii) an actuator configured to be selectively actuated by a user, wherein the actuator includes a C-shaped coupling feature, wherein the C-shaped coupling feature comprises: (A) a cavity, (B) a first retention feature facing the second direction, and (C) a second retention feature facing the first direction, wherein the first and second retention features of the first and second body portions are retained within the cavity using the first and second retention features of the C-shaped coupling feature.

EXAMPLE 17

A surgical stapler comprising: (a) a first elongate member that includes a distal portion that supports an anvil surface, wherein the anvil surface includes a plurality of staple forming pockets; (b) a second elongate member that includes a distal portion configured to receive a staple cartridge; (c) a clamp member operable to releasably clamp the first elongate member against the second elongate member; and (d) a firing assembly, wherein the firing assembly is translatable from a first longitudinal position to a second longitudinal position to fire the staple cartridge when the first elongate member is clamped against the second elongate member, wherein the firing assembly comprises: (i) a slider comprising first and second body portions that are fixably coupled together, wherein the slider includes a first coupling feature, and (ii) an actuator configured to be selectively actuated by a user, wherein the actuator includes a second coupling feature configured to be retained by the first coupling feature of the slider.

EXAMPLE 18

The surgical stapler of Example 17, wherein the first and second body portions are fixably coupled together using at least one of an adhesive, a press-pin feature, or an ultrasonic weld.

EXAMPLE 19

The surgical stapler of any one or more of Examples 17 through 18, wherein at least one of the first and second body portions includes a metal substrate and a polymeric overmold.

EXAMPLE 20

The surgical stapler of any one or more of Examples 17 through 19, wherein adhesive or a press-pin feature is disposed between the first and second body portions.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No. 15/889,374, entitled "Features to Align and Close Linear Surgical Stapler," filed on Feb. 6, 2018, issued as U.S. Pat. No. 10,932,781 on Mar. 2, 2021; U.S. application Ser. No. 15/889,376, entitled "Releasable Coupling Features for Proximal Portions of Linear Surgical Stapler," filed on Feb. 6, 2018, issued as U.S. Pat. No. 10,898,197 on Jan. 26, 2021; U.S. application Ser. No. 15/889,388, entitled "Firing Lever Assembly for Linear Surgical Stapler," filed on Feb. 6, 2018, issued as U.S. Pat. No. 10,874,398 on Dec. 29, 2020; U.S. application Ser. No. 15/889,390, entitled "Clamping Mechanism for Linear Surgical Stapler," filed on Feb. 6, 2018, issued as U.S. Pat. No. 10,687,819 on Jun. 23, 2020; and/or U.S. application Ser. No. 16/410,006, entitled "Actuator Support Structure for Surgical Stapler," filed on May 13, 2019, issued as U.S. Pat. No. 11,166,715 on Nov. 9, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, mate-

We claim:
1. A surgical stapler comprising:
(a) a first elongate member having a distal portion that supports an anvil surface, wherein the anvil surface includes a plurality of staple forming pockets;
(b) a second elongate member having a distal portion configured to receive a staple cartridge;
(c) a clamp member operable to releasably clamp the first elongate member against the second elongate member; and
(d) a firing assembly, wherein the firing assembly is translatable from a first longitudinal position to a second longitudinal position to fire the staple cartridge when the first elongate member is clamped against the second elongate member, wherein the firing assembly comprises:
(i) a slider that includes a first coupling feature, wherein the slider extends along a longitudinal axis that defines first and second lateral sides of the slider, and
(ii) an actuator configured to be selectively actuated by a user, wherein the actuator includes a second coupling feature configured to continuously capture the first coupling feature of the slider within a cavity defined by the second coupling feature as an entirety of the actuator moves between first and second lateral positions, wherein in the first lateral position the entirety of the actuator is disposed on the first lateral side of the slider, and wherein in the second lateral position the entirety of the actuator is disposed on the second lateral side of the slider.

2. The surgical stapler of claim 1, wherein the second coupling feature is a C-shaped coupling feature that includes the cavity, wherein the cavity is configured to receive the first coupling feature.

3. The surgical stapler of claim 2, wherein the C-shaped coupling feature includes first and second opposing projections configured to securably receive and maintain the first coupling feature within the cavity.

4. The surgical stapler of claim 3, wherein relative spacing between the first and second opposing projections of the C-shaped coupling feature are configured to securably receive and maintain the first coupling feature within the cavity.

5. The surgical stapler of claim 2, wherein the C-shaped coupling feature is integrally formed together as a unitary piece.

6. The surgical stapler of claim 2, wherein the first coupling feature of the slider is configured to guide the C-shaped coupling feature between the first lateral side of the slider and the second lateral side of the slider.

7. The surgical stapler of claim 1, wherein the slider includes first and second body portions.

8. The surgical stapler of claim 7, wherein the first coupling feature includes first and second coupling portions of the first and second body portions.

9. The surgical stapler of claim 8, wherein the second coupling feature is a C-shaped coupling feature that forms a cavity, wherein the first and second coupling portions include first and second opposing retention features that are received within the cavity of the second coupling feature.

10. The surgical stapler of claim 7, wherein at least one of the first and second body portions includes a metal substrate and a polymeric overmold.

11. The surgical stapler of claim 7, wherein the first and second body portions are coupled together using at least one of an adhesive, a press-pin feature, or an ultrasonic weld.

12. The surgical stapler of claim 7, wherein at least one ultrasonic weld is disposed between the first and second body portions.

13. A surgical stapler comprising:
(a) a first elongate member having a distal portion that supports an anvil surface, wherein the anvil surface includes a plurality of staple forming pockets;
(b) a second elongate member having a distal portion configured to receive a staple cartridge;
(c) a clamp member operable to releasably clamp the first elongate member against the second elongate member; and
(d) a firing assembly, wherein the firing assembly is translatable from a first longitudinal position to a second longitudinal position to fire the staple cartridge when the first elongate member is clamped against the second elongate member, wherein the firing assembly comprises:
(i) a slider comprising:
(A) a first body portion that includes first and second arms, wherein each of the first and second arms of the first body portion includes a first projection extending in a first direction, and
(B) a second body portion that includes first and second arms, wherein each of the first and second arms of the second body portion includes a second projection extending in a second direction that is opposite the first direction, and
(ii) an actuator configured to be selectively actuated by a user, wherein the actuator includes a C-shaped coupling feature, wherein the C-shaped coupling feature comprises:
(A) a cavity,
(B) a first projection extending in the second direction, and
(C) a second projection extending in the first direction, wherein the first and second projections of the first and second body portions are retained within the cavity using the first and second projections of the C-shaped coupling feature.

14. A surgical stapler comprising:
(a) a first elongate member having a distal portion that supports an anvil surface, wherein the anvil surface includes a plurality of staple forming pockets;
(b) a second elongate member having a distal portion configured to receive a staple cartridge;
(c) a clamp member operable to releasably clamp the first elongate member against the second elongate member; and
(d) a firing assembly, wherein the firing assembly is translatable from a first longitudinal position to a second longitudinal position to fire the staple cartridge when the first elongate member is clamped against the second elongate member, wherein the firing assembly comprises:
(i) a slider comprising a first coupling feature, the first coupling feature comprising:
(A) a first projection extending in a first direction, and
(B) a second projection extending in a second direction that is opposite the first direction; and (ii) an actuator configured to be selectively actuated by a user, wherein the actuator includes a second coupling feature, the second coupling feature comprising:
(A) a first projection extending in the second direction, and
(B) a second projection extending in the first direction, wherein the first and second projections of the actuator are configured to continuously capture the first and second projections of the first coupling feature of the slider as an entirety of the actuator, including the second coupling feature, is moved along the first and second projections of the slider between a first lateral side of the slider and a second lateral side of the slider.

15. The surgical stapler of claim 14, wherein the slider comprises first and second body portions that are fixably coupled together using at least one of an adhesive, a press-pin feature, or an ultrasonic weld.

16. The surgical stapler of claim 15, wherein the slider further comprises a third body portion that includes a first projection extending in the first direction and a second projection extending in the second direction.

17. The surgical stapler of claim 16, wherein the third body portion includes a neck portion configured to be selectively received within a space between the first and second projections of the C-shaped coupling feature.

18. The surgical stapler of claim 1, the first coupling feature comprising:
(A) a first projection extending in a first direction, and
(B) a second projection extending in a second direction that is opposite the first direction.

19. The surgical stapler of claim 14, wherein the slider extends along a longitudinal axis, wherein the second coupling feature is configured to continuously capture the first coupling feature of the slider as the entirety of the actuator, including the second coupling feature, is moved between first and second lateral positions, wherein in the first lateral position the entirety of the actuator, including the second coupling feature, is positioned on the first lateral side of the slider, and wherein in the second lateral position the entirety of the actuator, including the second coupling feature, is positioned on the second lateral side of the slider.

20. The surgical stapler of claim 14, wherein the first projection of the actuator is configured to be in continuous contact with the first projection of the slider between the first and second lateral sides of the slider, wherein the second projection of the actuator is configured to be in continuous contact with the second projection of the slider between the first and second lateral sides of the slider.

* * * * *